US009821345B2

(12) United States Patent
Sterkel

(10) Patent No.: US 9,821,345 B2
(45) Date of Patent: Nov. 21, 2017

(54) APPARATUS AND METHOD FOR SORTING OBJECTS BY REBOUND BEHAVIOR

(71) Applicant: Glenn Sterkel, South Elgin, IL (US)

(72) Inventor: Glenn Sterkel, South Elgin, IL (US)

( * ) Notice: Subject to any disclaimer, the term of this patent is extended or adjusted under 35 U.S.C. 154(b) by 0 days.

(21) Appl. No.: 15/341,501

(22) Filed: Nov. 2, 2016

(65) Prior Publication Data

US 2017/0128986 A1      May 11, 2017

Related U.S. Application Data

(60) Provisional application No. 62/252,025, filed on Nov. 6, 2015.

(51) Int. Cl.
*B07C 5/00*        (2006.01)
*B07C 5/34*        (2006.01)
*G01N 3/40*        (2006.01)

(52) U.S. Cl.
CPC .................. *B07C 5/34* (2013.01); *G01N 3/40* (2013.01); *B07C 2501/0018* (2013.01)

(58) Field of Classification Search
CPC .......................... B07C 5/34; B07C 2501/0018
USPC ............. 209/637, 638, 640; 73/12.01, 12.06, 73/12.13
See application file for complete search history.

(56) References Cited

U.S. PATENT DOCUMENTS

| 2,740,287 | A |   | 4/1956  | Gindraux |  |
|-----------|---|---|---------|----------|--|
| 3,038,330 | A | * | 6/1962  | Criche   | G01N 3/52 73/79 |
| 3,411,626 | A |   | 11/1968 | Kreamer  |  |
| 3,625,052 | A | * | 12/1971 | Jones    | G01N 3/52 73/12.11 |
| 4,006,626 | A | * | 2/1977  | Ruzicka  | G01N 3/52 73/12.02 |
| 4,195,735 | A |   | 4/1980  | Facchinelli |  |
| 4,509,362 | A |   | 4/1985  | Lyons    |  |
| 4,876,658 | A |   | 10/1989 | Hass     |  |
| 5,197,473 | A | * | 3/1993  | Fedorov  | A61B 3/152 600/398 |
| 5,245,862 | A | * | 9/1993  | Zeiss    | G01N 3/52 73/12.01 |
| 6,571,600 | B2| * | 6/2003  | Bissonnette | A63B 47/008 73/12.02 |
| 2004/0206156 | A1 | * | 10/2004 | Barr | G01N 3/303 73/12.01 |

(Continued)

FOREIGN PATENT DOCUMENTS

SU         1395391      *   7/1986    ............... B07C 5/34

*Primary Examiner* — Terrell Matthews
(74) *Attorney, Agent, or Firm* — Ladas & Parry LLP

(57) ABSTRACT

A sorting apparatus and method are for sorting objects based on the objects' rebound from a surface. An automatic sorting apparatus based on objects' rebound from a surface, comprising: a cylinder disposed on top of the apparatus to hold and drop an object vertically downside with a force of gravity; a rebound impact surface disposed vertically downside of the cylinder; a rebound height sorting sensor configured to measure an apex of the rebounded object; a light source; a projection screen; and a sorter configured to sort the object based on the apex of the rebounded object, wherein the light source projects the object on the projection screen, and the rebound height sorting sensor detects the apex of the rebounded object based on positions of a shadow of the object on the projection screen.

24 Claims, 5 Drawing Sheets

(56) References Cited

U.S. PATENT DOCUMENTS

2009/0031783 A1\* 2/2009 Fukushima ............ G01N 3/303
　　　　　　　　　　　　　　　　　　　　　　　73/12.06
2009/0082122 A1\* 3/2009 Kellogg ............. A63B 69/3614
　　　　　　　　　　　　　　　　　　　　　　　473/222

\* cited by examiner

APPARATUS AND METHOD FOR SORTING OBJECTS BY REBOUND BEHAVIOR

RELATED APPLICATIONS

The present patent document claims the benefit of the filing date under 35 U.S.C. §119(e) of Provisional U.S. Patent Application Ser. No. 62/252,025, "APPARATUS AND METHOD FOR SORTING OBJECTS BY REBOUND BEHAVIOR," filed Nov. 6, 2015, which is hereby incorporated by reference.

TECHNICAL FIELD

The disclosed embodiments relate generally to a sorting apparatus and method, and more particularly, to an apparatus and method for sorting objects based on the objects' rebound from a surface.

BACKGROUND OF THE INVENTION

Various widely enjoyed sports utilize objects (typically balls) that rebound from hard surfaces. These objects are mass produced, have a limited lifespan, and as they wear out are discarded. Many sports have standard guidelines stipulating how well the equipment utilized in the sport should perform, thus setting limits on when an object of play is no longer acceptable for use in sanctioned competition.

Tennis provides the best example here. The International Tennis Federation (ITF) is a governing body having one such standard for tennis balls. The tennis ball must satisfy a number of criteria including basic performance characteristics to ensure consistency and fairness in competition. The standards are normally applied to new balls to ensure manufactured product meets the expected quality for tournament play, however these same guidelines provide an excellent standard against which used balls can be compared, as they degrade with age and use. Players want to practice and play recreationally with quality balls without having to open a new canister every time they step on the court. The bounce of the ball is a critical performance characteristic for tennis, where every shot is allowed (and at most times required) to bounce off the court surface. This bouncing off a surface will henceforth be referred to as "rebound" (more complete definition below).

The ability of a ball to rebound well after impacting a surface is the most common test players use to determine that a tennis ball is fit for play. If a ball appears to have lost its ability to rebound to a minimally tolerable height, it is retired from the game, and most of these are discarded in the trash. It is estimated that between 300 and 500 million tennis balls are discarded every year (based on manufactured quantity estimates). Samples of discarded balls taken from indoor tennis club practice carts show that as many as 80% of the balls discarded might still meet the ITF Rebound standard for play if they were tested (other criteria of the ITF standard notwithstanding). However, the process for testing rebound performance of a tennis ball per the ITF standard requires specialized testing equipment and is a time and labor intensive task most people or clubs are not prepared to perform.

This problem is experienced by recreational players and professionals alike, and magnified further for tennis facilities who utilize and manage large quantities of balls. So there are few options available to check a large batch of balls: tediously bounce each ball to see if it is still play worthy, or do a hand "squeeze test" (proven inaccurate), or use one or several commercially available devices to squeeze them (also highly inaccurate). The most common choice is to just replace entire batches of balls periodically to ensure consistent quality. This results in far too many balls being discarded into landfills where they take an estimated 400 years to decompose. It is also a waste for some to be discarded before they have been exhausted of their useful life. This situation is the main reason many perfectly usable tennis balls are not widely re-used. It is simply too difficult and costly to separate the good balls from the bad ones.

Because of this, used balls are rarely collected and less often sorted. Where used balls are accumulated for resale, they are normally sold as-is with the good and bad mixed together which only tends to reduce their value in the marketplace.

There is no industry solution for how to accurately determine which balls in a large batch of balls are compliant with rebound guidelines, nor has any prior art been found to address how to perform such a determination (whether accurate or inaccurate) in any efficient or cost-effective manner. The need clearly exists for an easy and inexpensive way to separate balls into a number of rebound performance grades. A solution to sorting used balls creates a new incentive in the recycling industry to collect large batches of balls which can then be properly and affordably recycled. Such capability makes possible the much desired environmental conservation practices, which are: REDUCE, REUSE, and RECYCLE.

BRIEF SUMMARY OF THE INVENTION

The above deficiencies and other problems associated with sorting used balls are reduced or eliminated by the disclosed automatic sorting apparatus and method. The apparatus and method described herein provide a fast, accurate, and reliable process to sort objects by how well they rebound from a surface. The apparatus and method can be applied to any object, where one commercially viable application is for balls employed in various sports, especially sports such as tennis or racquetball whose balls have rebound characteristics standardized and tend to degrade with use and age. In such applications, the invention herein described reduces inefficiency and lowers the cost and effort of identifying and sorting playable from non-playable balls. It also enables a system of quality grading (quality being defined here as rebound performance) to allow used ball resellers to target the consumer demand for a particular level of performance. This ability to grade used balls thereby serves to maximize the commercial value of each ball when sold in the marketplace. Taking these factors together, one can see how the ability to easily sort and grade batches of tennis balls enables all the aforementioned environmental conservation practices; it helps REDUCE the needed ball quantities produced per player, allows players to REUSE existing resources by extending use of balls for a longer time, and creates an incentive to RECYCLE by enabling a large scale and financially sustainable recycling business model through affordable material sorting.

In one aspect of the invention, an automatic sorting apparatus based on objects' rebound from a surface, comprising: an object holder disposed on top of the apparatus to hold and drop an object vertically downside with a force of gravity; a rebound impact surface disposed vertically downside of the object holder; a rebound height sorting sensor configured to measure the first occurring apex of the rebounded object; a light source; a projection screen; and a sorter configured to sort the object based on the apex of the rebounded object, wherein the light source projects the object on the projection screen, and the rebound height sorting sensor detects the apex of the rebounded object based on positions of a shadow of the object on the projection screen.

In another aspect of the invention, a method for automatically sorting objects based on the objects' rebound from a surface, comprising: dropping an object; emitting light rays to the rebounded object on a project screen at a right angle; acquiring a plurality of the object's positions based on positions of a shadow of the rebounded object on the project screen; detecting moving shadow edges by scanning the moving shadow edges; determining a peak rebound position of the object based on the detected edges; and directing the rebounded object into a selected space of a plurality of independent sorting spaces, wherein the object is directed to the selected space based on the determined peak rebound position of the object.

BRIEF DESCRIPTION OF THE FIGURES (NON-LIMITING EMBODIMENTS OF THE DISCLOSURE)

For a better understanding of the aforementioned embodiments of the invention as well as additional embodiments thereof, reference should be made to the DETAILED DESCRIPTION below, in conjunction with the following drawings in which like reference numerals refer to corresponding parts throughout the figures.

DETAILED DESCRIPTION

Figure 1:
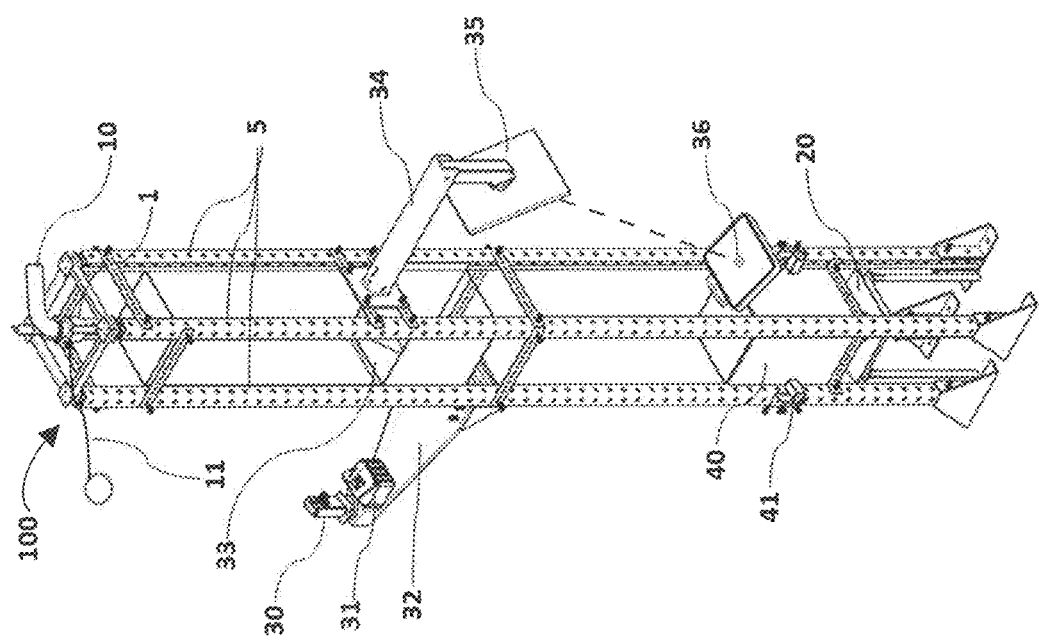
FIG. 1 shows a perspective view of an embodiment of the present invention.

Reference will now be made in detail to embodiments, examples of which are illustrated in the accompanying drawings. In the following detailed description, numerous specific details are set forth in order to prove a thorough understanding of the present invention. However, it will be apparent to one of ordinary skill in the art that the present invention may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first gesture could be termed a second gesture, and, similarly, a second gesture could be termed a first gesture, without departing from the scope of the present invention.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Four terminologies used in the description of the invention herein are defined as below:

REBOUND: as used herein as a verb, is defined as to spring or bounce back after impact with a surface, and as a noun, is defined as a springing or bounding back after impact with a surface. In this sense, the term is also used as an adjective to uniquely describe the following nouns in the context of a rebounding object: height, position, distance, performance, specification, response, characteristic, and grade.

REDUCE: as used herein as an environmental stewardship strategy, is defined as the first and most effective component of the waste hierarchy i.e. reducing waste created. Consumers are encouraged to reduce their waste by purchasing in bulk, buying items with less packaging and switching to reusable instead of single-use items. Businesses can adopt manufacturing methods that require fewer resources and generate less waste. In addition to benefiting the environment, these efforts often offer consumers and businesses the financial incentive of lower expenses in purchases.

REUSE: as used herein as an environmental stewardship strategy, is defined as: in circumstances where waste is inevitable, a product can immediately be reused while it retains its value for the purpose for which it was created. For example, consumers can purchase used items from thrift stores or online discount sites to reduce the number of such items being discarded. Consumers have a financial incentive here as well, as used items are typically far cheaper than buying new.

RECYCLE: as used herein as an environmental stewardship strategy, is defined as: When waste is eventually discarded, segregating items from other waste to separate raw materials which can be used instead of extracting new material resources from the environment. Recyclables include glass, rubber, aluminum, cardboard and a surprising array of other materials.

Embodiments of the present invention include a fast, accurate, and reliable example to sort a plurality of objects by how each one rebounds from a surface. The invention embodies methods to control, detect, measure, and sort the plurality of objects while in continuous fluid sequence. The user gains an accurate representation of each object's dynamic response to the environment immediately after the initial rebound of the object reaches an apex, and then immediately sees each object sorted into a group of similarly responding objects according to their rebound performance.

The embodiments have been demonstrated to perform the rebound sorting function for the example tennis ball in less than 2.3 seconds, which is the time it takes for a standard tennis ball to drop from a sufficient height (100 inches/254 cm), rebound up to a peak, then fall back to the ground. The embodiment is capable of sorting over 1600 tennis balls per hour into 4 distinct grades, using less than 500 watts of electrical power. Parallel embodiments may be used to scale up the throughput capacity.

It should be appreciated that the apparatus 100 is only one example of an automatic sorting apparatus 100, and the apparatus may have more or fewer components than shown, may combine two or more components, or may have a different configuration or arrangement of the components.

The embodiment of the present invention includes a fully automated process which, under prescribed environmental conditions, takes a large quantity of balls, loads them one after the other into a processing machine which delivers (preferably drops) each ball in a controlled manner (preferably from a specified height) to impact a solid surface. After impact and rebound from the surface during the ball's rebound, the process uses a video sensor to scan and measure the position of the ball at the apex of its rebound path, and as the ball consequently descends to the space below, the process redirects the ball into one of several locations based on the measurements taken. The balls are thus sorted into defined grade levels according to relative rebound performance.

Figure 2A:
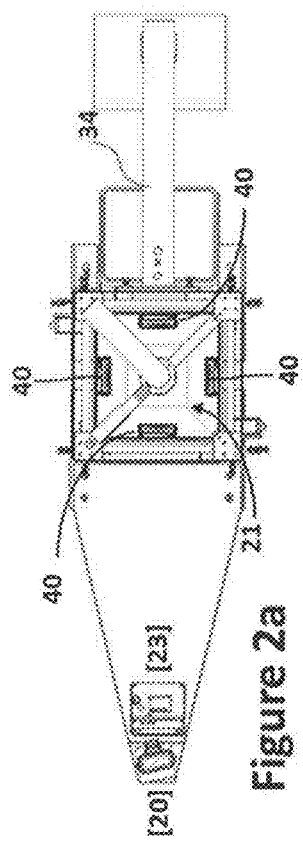
FIG. 2a shows a top view looking down on the general embodiment.
Figure 2B:
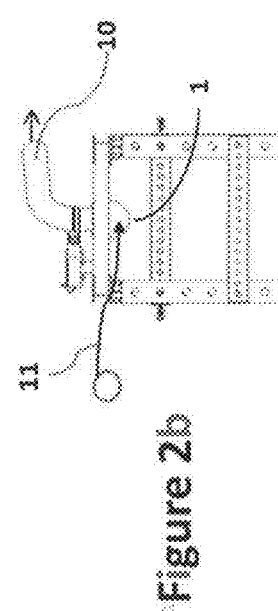
FIG. 2b shows the top starting and dropping section of the general embodiment.
Figure 2C:
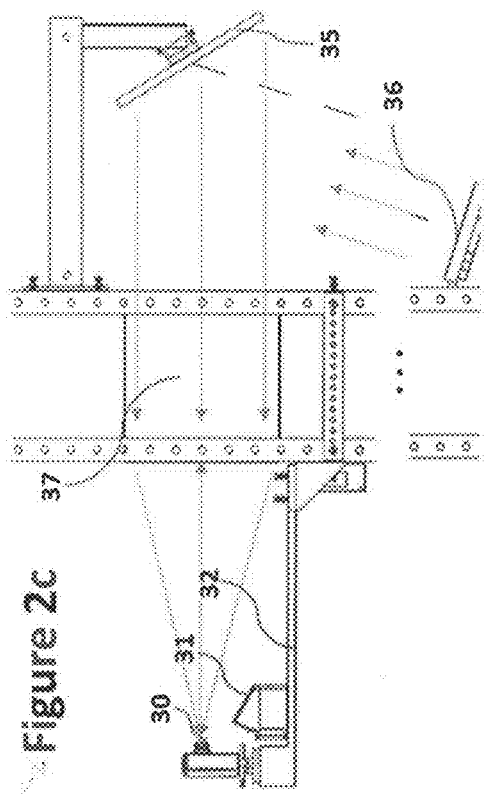
FIG. 2c shows the middle measurement section of the general embodiment.
Figure 2:
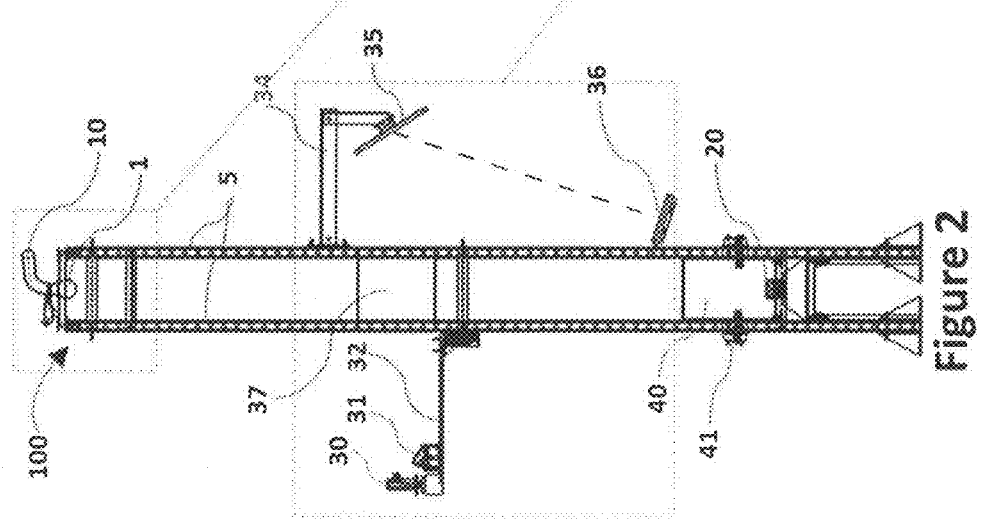
FIG. 2 shows a side profile of the general embodiment indicating where top and center sections are expanded to show detail.
Figure 3:
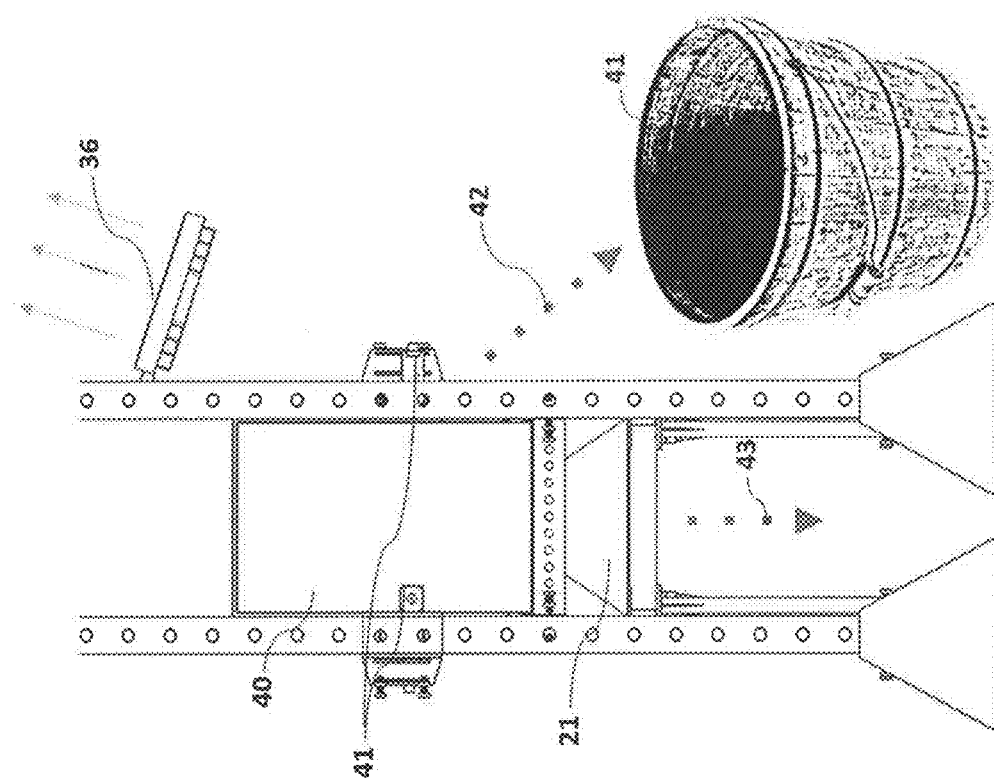
FIG. 3 shows a side profile of the general embodiment indicating where the bottom section is expanded to show detail.

FIGS. 1, 2, and 3 show one embodiment of the automatic sorting apparatus 100. The automatic sorting apparatus 100 comprises three sections: top starting and dropping section, middle measurement section, and bottom sorting section. The three sections are connected by four vertically elongated frames 5. However, the three sections may be connected by other ways. For example, the three sections may connected by two long panels. The top starting and dropping section, described in FIG. 2b in detail, may include an object dropper 10 and a feeding system 11. The middle measurement section, described in FIG. 2c in detail, may include a video sensor 30, a computing device 31, a supporting stand 32, a projection screen 33, a reverse L-shape holder 34, a mirror 35, and a light source 36. The bottom sorting section, described in FIG. 3a in detail, may include an impact surface 20, sorting gates 40, electric push solenoids 41, and sorting spaces 41.

FIG. 2b depicts the top starting and dropping section of the automatic sorting apparatus 100 in detail. The ball 1 in this embodiment is a ball used in the sport of tennis. Although tennis balls provide an example, the invention can apply to any other object that is subject to an expected or standardized level of rebound performance. Examples of other sports with similar conditions, and with governing bodies like the International Tennis Federation (ITF) may include but are not limited to: United States Tennis Association (USTA), International Racquetball Federation (IRF), England Squash, World Dodgeball Federation (WDF).

The feeding system 11 takes a large quantity of balls, loads them one after the other to the object dropper 10. The feeding system 11 feeds a ball 1 to the object dropper 10 immediately after a previous ball has dropped clear, and the dropper 10 releases a ball after a previous ball has egressed the space between the object dropper 10 and the impact surface 20. The feeding system 11 may comprise an elongated cylinder or track including a plurality of balls and a flap or other controlling device to feed one ball at a time to the object dropper 10. The elongated cylinder and the flap may be other forms to feed a plurality of balls to the object dropper 10. For example, the elongated cylinder may be simple elongated two or more wires to make the balls to move to the object dropper 10. The flap may also be elongated wires to block and feed a ball to the object dropper 10. The feeding system 11 may also comprise a system of lifting apparatuses to elevate balls from a lower position up to the feeding system 11 or directly to the object dropper 10. The lifting apparatuses may be mechanical forms such as a pneumatic pressure tube, an Archimedes screw, or a continuous series of elevated compartments or shelves, to contain the balls and transport them from a container or other location to the sorting system. Typical transport mechanisms such as conveyors or ball tracks may also be comprised in the feeding system 11.

The object dropper 10 is placed at the 100 inches/254 centimeters height from the impact surface 20. However, it should be understood that the object dropper may be placed at a different height. The object dropper 10 may be a cylinder to hold the ball 1 by exerting an attractive upward force on the ball preventing it from falling due to gravity and discontinue the attractive force thus releasing the ball to fall freely with negligible rotational motion. In this case, the diameter of the cylinder is smaller than that of the ball. The cylinder 10 applying an attractive force may be a vacuum canister or other means of creating vacuum pressure to hold the object for a controlled release. However, the diameter of the cylinder 10 may be bigger than that of the ball 1. The cylinder 10 may be connected to or part of the feeding system 11. Instances of the ball 1 are provided through the cylinder one after the other. The object dropper 10 may hold the ball 1 by a device to grab and release the ball. The feeding system 11 may directly drop the ball 1 vertically downward to the impact surface 20. The ball 1 falls vertically down toward the impact surface 20 and rebounds. Then, the ball 1 rebounds to a peak. The object dropper 10 and impact surface 20 are aligned such that the ball 1 having sufficient rebound energy will rebound vertically to arrive at a peak within the middle measurement section of the apparatus where its position may be surveyed as it enters the measurement space 37. If the ball 1 does not have sufficient rebound energy to reach the measurement space 37, the automatic sorting apparatus 100 will sort the ball 1 to the lowest height sort group, or reject as an error if sorting cannot be performed.

FIG. 2c illustrates the middle measurement section of the automatic sorting apparatus 100 in detail. A light source 36 is placed at or near the bottom of the apparatus 100. A point light source with a uniform back reflector is preferably used for the light source 36 to concentrate and direct light toward the mirror 35 which in turn creates near-parallel rays through the measurement space 37 to produce a clear shadow of an object present within the measurement space 37 on the projection screen 33. As a point light source, a light-emitting diode may be used. The light source 36 may also include but not be limited to: a screen projector, laser, and light bulb. The light source 36 produces light rays toward the mirror 35. The light rays from the light source 36 are emitted in a disperse way. However, the light rays reflected from the mirror are dispersed only in a direction through a measurement space 37 and thus, the light rays proceed through a measurement space 37 to the projection screen 33 in a near-parallel way.

The projection screen 33 is placed at a right angle to the light rays from the mirror 35 to the projection screen 33. The rebounded ball 1 in the measurement space 37 makes a shadow on the projection screen 33. Since the light rays move in a near-parallel way, the height of the shadow on the projection screen 33 is sufficiently the same in terms of differentiating height for sorting, as the real height of the ball 1, irrespective of where the ball is positioned laterally in the measurement space 37. The alignment of the light path allows a ball 1 shadow to represent the actual height position of a ball 1 in the measurement space 37. The projection screen 33 is made of a material for the shadow of the ball 1 to be visible on the other side of the projection screen 33 on which the light rays are not directly projected. The projection screen 33 may be a piece of paper or a translucent or semitransparent material such as a plastic lamination sheet, or any material that produces contrast between shadow and background on the side opposite the side directly illuminated. The shadow of the ball 1 on the other side of the projection screen 33 is scanned by a video sensor 30.

The following is a discussion of details of video sensor 30 scanning. The video sensor 30 and the computing device 31 are placed external to the measurement space 37 for the purpose of acquiring a plurality of measurements of the ball's rebound behavior when the ball is expected to be within the measurement space 37. The supporting stand 32 is tightened to the elongated frames 5 and holds the video sensor 30 and computing device 31 at the outside of the measurement space 37. However, the video sensor 30 and the computing device 31 may be tightened in a different way. The video sensor 30 can provide both accurate spatial and timing data. The embodiment takes advantage of the precise time reference inherent in the sensor video scan data and the processing device's ability to determine the object's position at a precise time from the sensor data (horizontal line and vertical frame scan synchronization) to accurately set the timing of when a sorting gate is activated. The computing device 31 does this by computing the necessary time delay between acquiring each object's peak rebound position and when the sorting gate should be activated. The time at which the peak position occurred as derived from the video sensor frame data, and delay times computed from the resulting distance the object must free-fall due to gravity between that peak and the sorting gates below.

The computing device 31 may include timing routines for controlling all physically automated events from said object drop to said sorting gate activation such that said activation is correctly timed and occurs reliably; error routines for responding to both expected and unexpected events that will or may occur in software execution: external output to provide an operator data generally necessary to manage or take advantage of said acquired results; input devices providing an operator the means to manually start, stop, or pause the process; data memory for recording relevant data for each object processed for the purpose of controlling events and event timing to automate operation; routines for counting the number of balls thus dropped and counting the number directed into each sorting group, and counting the number of failures or error which may occur; data storage for providing a historical record of all process actions, event times, and measurement results as the process is repeated; devices for providing status indications visibly or audibly to aid in monitoring the state of operation, including warning when sort group bins begin to near capacity; routines for pausing when sort counts reach set thresholds so that sort collection bins can be emptied and replaced; error detection routines for stopping the process in the event of various potential malfunctions; input/output devices providing an operator the means to set, save, and restore system parameters.

The computing device 31 may also be positioned in a different place. The video sensor 30 scans the movement of the shadow of the rebounded ball 1 on the screen 33. The computing device 31 begins to read data from the video sensor 30 as it scans for shadow on the screen. This read is started by the computing device 31 based on when the rebounded ball 1 is expected to enter the measurement space 37 after an expected time. The expected time is estimated from the ball drop time and time required for the ball to fall, impact, and rebound up to the measurement space. Time from start of drop through rebound up to the bottom of the measurement space 37 is substantially constant due to gravity (varies slightly by air resistance to the ball's surface and amount of energy exchanged at impact 20). Measurements are preferably taken on the first rebound of the ball, but it should be understood that the measurements may also be taken after the ball has bounced more than 1 time (e.g., measuring the second bounce) Once the computing device 31 begins receiving data, it synchronizes with the frame timing of the video sensor 30 and collects multiple frames of image data to process, continuing until a full set of at least 5 frames has been collected. The frame rate and number of frames is determined by predetermining the time that the ball 1 to sort would be present in the measurement space 37, given the expected range of performance for the type of the ball. The computing device 31 evaluates the image data in software to determine the peak height of the ball reached and how long it should wait before activating the sorting gate 40 that corresponds to the measurement. During this process, the computing device 31 also records all relevant results and provides output to the operator. Both the peak height and the time when the peak occurred are used to determine an appropriate time to open the gate 40 using basic object free-fall formulas.

The computing device 31 processes the image of the projected shadow of the object with a single data bit from the digital image data stream sent from the video sensor 30, to determine where the shadow of the ball 1 appears on the projection screen 33. The data is received as the video sensor 30 scans across and down the two dimensional image space where the shadow is projected, with scan timing synchronized both vertically and horizontally to attain pixel rates necessary to gain sufficient spatial accuracy of the vertical location of the shadow. Thus, it is important to align a light source 36 and optics to produce near-parallel light rays through the measurement space to the projection screen 33, to ensure accurate ball height calculations can be derived from the shadow regardless of where the object is positioned laterally within the measurement space 37. It is further necessary to position the video sensor 30 with respect to the projection screen 33 such that it focuses on the screen 33 and is able to scan the screen area in such a way as to enable the computing device 31 to correlate each vertical scan line with a corresponding height measurement for the object. Such positioning of the video sensor 30 may be statically mounted or set dynamically during calibration procedures by a position controller controlled by the computing device 31. The computing device 31 determines the peak height of the ball by detecting moving shadow edges by scanning the edges as the shadow decelerates upward to the peak and applying a row-by-row random-walk algorithm to catch the peak of a bottom of the shadow. Other algorithms may also be used to obtain similar results.

The computing device 31 may implement the functions above by an algorithm described below.

Main Algorithm

```
START
{
Initialize program, setup hardware I/O
calibrate video sensor (with a calibration object placed in center of measurement
space)
        set sensor configuration
        set focus and gain for ambient light/shadow levels
        Run calibration scan to set detection thresholds and calibrate height
measurement
display calibration results to user to confirm readiness
get input from user to set run mode
get saved long term count data
Ready to sort [upon release of pause switch]
(while paused, user can activate diagnostics or adjust sort counts if necessary)
     OPERATION REPEATED FOR EACH BALL {
         initialize sensor for new scan
         release ball
         wait for rebound to screen
         read and store scan data from sensor while ball is expected to appear
on screen (multiple frames)
             [see VIDEO SCAN algorithm in the next paragraph- peak row
reached on rebound is returned]
         analyze stored line data from all frames to validate measurement (exit
and do not sort if invalid)
         determine timing of when the highest peak occurred
         calculate how long to wait from peak occurrence to when the ball will
fall to the gate section below
             [calculates both which gate to activate and delay before gate
activation]
         wait the necessary calculated delay time [accounting also for
processing delays]
         activate selected gate
         increment sorting counts and generate notifications
         send ball data to serial port, light status indicators
         reset sorting cycle variables
} END REPEAT
(If stop button pressed during pause wait time, Exit sorting)
save long term count data to continue with on next run
END
```

VIDEO SCAN Algorithm

This routine scans the video to perform the shadow detection and calculations in real-time so the processor can record an accurate peak height and time the sorting gates to catch the ball when it falls

START

[camera module is always running and sending video bits to the processor]

Sync with video sensor's Vertical SYNC and Horizontal line reference (HREF) timing signals to detect a stream of "pixels".

[The bit stream received consists of the most significant bit of a 7 bit monochrome VGA video signal down sampled 8:1, with 60 lines vertical resolution, at approx. 14-20 frames/sec. Frame rate and thus the number of video frames taken while the ball 1 is expected to be within the measurement space 37, ensures the spatial resolution needed to determine the position of the ball 1 at its rebound peak.]

Wait for first full frame to start (this start delay is accounted for in later delay calculations)

Scan lines in frame down from top (per orientation of the sensor)

count the number of pixel bits in each row that are not shadow compare number of pixel bits in each line to baseline threshold (set in calibration)

if line has ball shadow, keep track of which shadowed line is the lowest for the frame repeat above for 5 or more frames, tracking which frame has the highest "lowest shadow line"

record the overall peak line for all frames store all frames of line data for diagnostic dump if requested return to main program

END

The computing device 31 communicates with the video sensor 30, the object dropper 10, and the sorter 41 using wires or a wireless network. The wireless network includes a wireless local area network (LAN) and/or a metropolitan area network (MAN), and other devices by wireless communication. The wireless communication my use any of a plurality of communications standards, protocols and technologies, including but not limited to Bluetooth, Wireless Fidelity (Wi-Fi) (e.g., IEEE 802.11a, IEEE 802.11b, IEEE 802.11g and/or IEEE 802.11n) or any other suitable communication protocol, including communication protocols not yet developed as of the filing date of this document.

The way to measure the peak of the rebounded ball 1 described above is just one example. The peak of the rebounded ball 1 may be measured by using a pressure measurement sensor before the rebounded ball 1 reaches the peak. To use the pressure measurement sensor, the rebounded ball 1 hits the pressure sensor with an upward force. The pressure sensor is placed without preventing the ball from falling to the rebound impact surface 20. Thus, the impact surface 20 has a slope so that the ball rebounds in a different direction from the true vertical way. According to the level of the pressure how hard the ball hits the sensor, one of the sorting gates 40 is opened.

The peak of the rebounded ball 1 may also be measured by using velocity and acceleration of the rebounded ball before the rebounded ball 1 reaches the peak. Using a force of gravity, the velocity right after rebound of the ball 1, and air resistance value of the ball, the peak height of the ball 1 can be calculated. Based on the calculated peak height of the ball 1, one of the sorting gate 40 is opened.

In this embodiment, there is a relationship between size and processing speed, due to the limited time available to complete the critical task of determining the sort before the object falls to the sorting gate mechanism. In general practice, the rebound specification distances stipulated by relevant governing bodies may constrain an embodiment to a structure of dimensions commensurate with those distance requirements, however any embodiment of any size may be envisioned that can perform the sorting function within the time constraints of a single rebound.

Figure 3A:
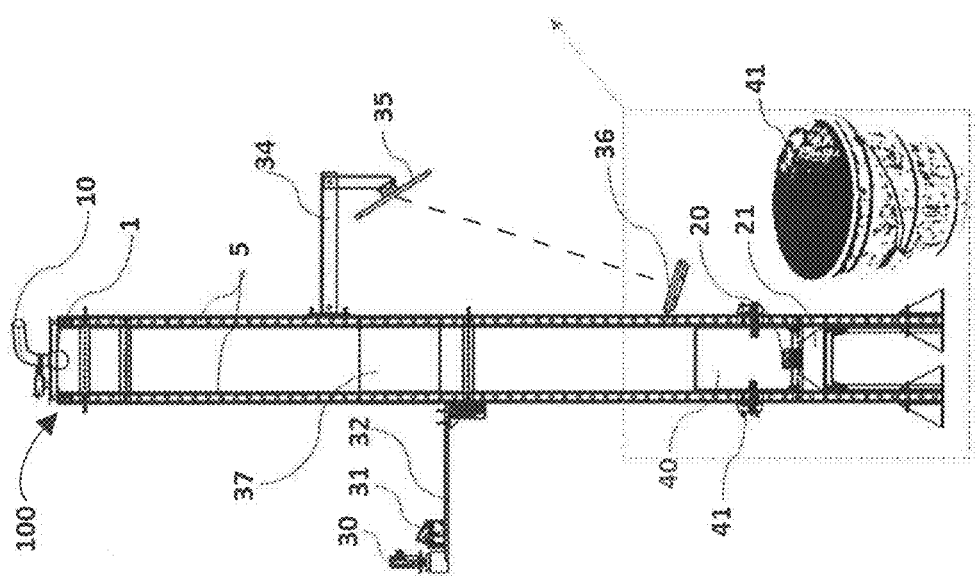
FIG. 3a shows the bottom sorting section of the general embodiment.

FIG. 3a illustrates the bottom section of the automatic sorting apparatus 100 in detail. When the ball 1 falls down from the object dropper 10, the ball 1 impacts the impact surface 20. The impact surface 20 is aligned in the path of the ball motion, formed in a manner which results in the ball always impacting the surface squarely on its first vertical descent in order to rebound into the measurement space 37 to have its peak rebound height measured and a selected sorting gate 40 activated below it. The impact surface 20 may further be formed to accommodate cases where the process fails to redirect the object out a sorting pathway. Forming the impact surface to slope down from center in a generally conical shape with a flat center portion creating the rebound impact surface 20 sized only slightly larger than object diameter, and relying upon small variations in both the rebound impact surface 20 and the ball's surface, random minor deflections from true vertical will occur which do not significantly affect the rebound performance of the object but will cause the ball 1 to miss and pass by the small impact surface on subsequent descents (the vast majority of the time this will be the case), thus allowing the object to pass into a "no-sort exit" 43 for cases where the object is not redirected by a sorting gate 40.

In the embodiment, a plurality of sorting gates 40 are aligned with the outer extents of the space which contains the ball in motion, such that one and only one sorting gate 40 can open at a time to redirect the path of an object, leaving no available space for an object to travel except through the space provided by the opening of the sorting gate 40. One of the sorting gates 40 is opened based on the spatial measurement values derived from the image data, analyzed and compared against multiple threshold values which are predetermined. Data is also collected against known calibrated conditions during process startup and used in setting up and calibrating the system to ensure accuracy. In order to perform a plurality of object sorts as rapidly as possible, the embodiment should choose one of a plurality of independent sorting spaces 41 to direct each ball 1 into within the time available between the acquisition of measurements and completion of the object's natural fall to the sorting mechanism that is positioned below. Such a requirement drives the size of the apparatus and the processing capabilities of the measurement and control devices. The plurality of independent openings with sorting gates 40 are positioned peripherally around the ball's path of motion. A sorting gate 40 may include a rigid flap mounted by spring loaded hinges such that the flap remains closed until such time as an activating device forces the flap to move to the open position then automatically return closed. The activating device may include a gate opening mechanism on each gate activated to open by means of an electric push solenoid 41 controlled by a device which can initiate an electrical signal to the solenoid.

Figure 4:
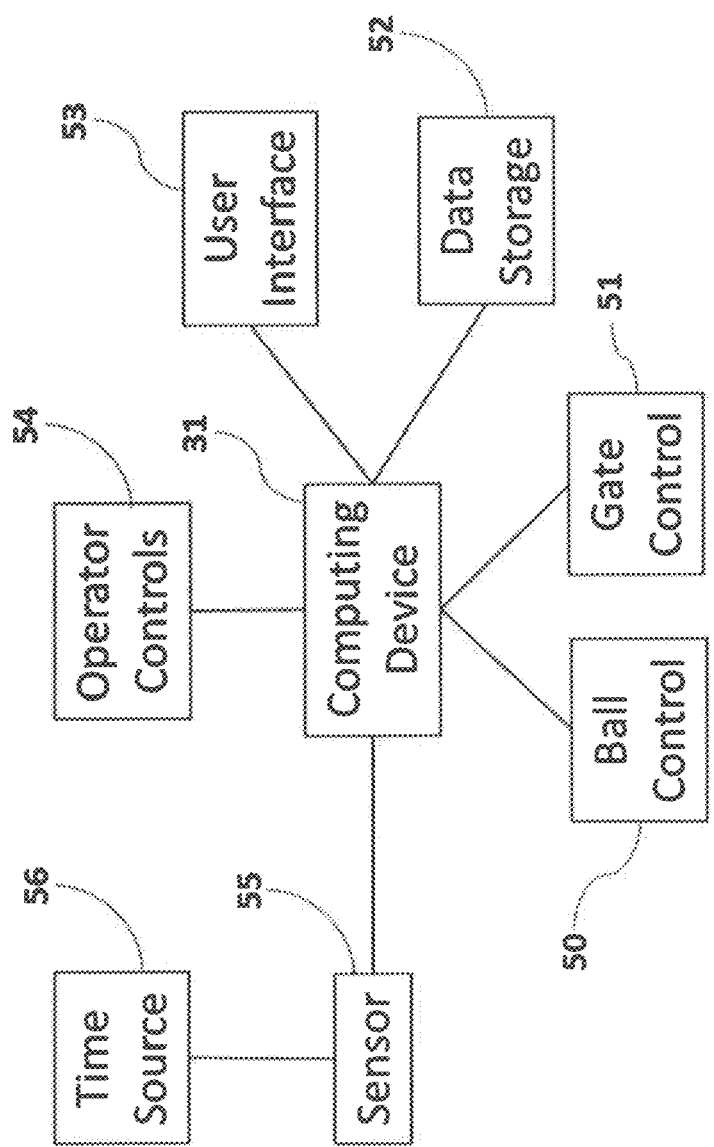
FIG. 4 illustrates the processing interactions involved in the general embodiment.

FIG. 4 illustrates a rebound sorter and processing interactions. The computing device 31 interacts with a ball control 50, gate control 51, user interface 52, data storage 53, operator controls 54, and sensor 55. The sensor interacts with a time source 56.

Figure 5:
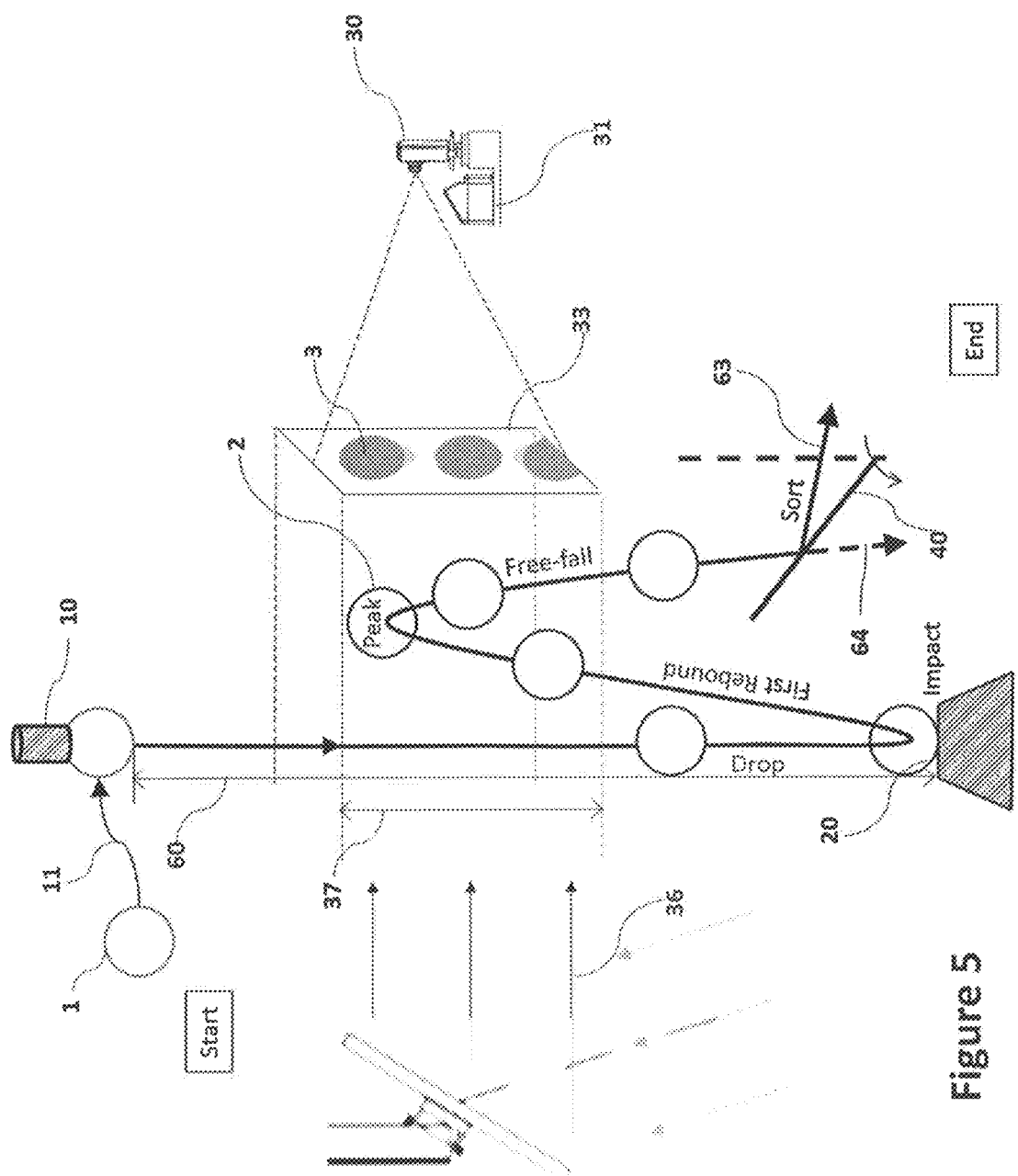
FIG. 5 illustrates the dynamic activity of a method of sorting according to an embodiment of the present invention.

FIG. 5 illustrates the dynamic activity of a method for automatically sorting objects based on the objects' rebound from a surface. The path is substantially vertical. Small deflection from true vertical occurs randomly. The deflection in FIG. 5 is exaggerated to provide ample space to show object flow. In an embodiment a method for automatically sorting objects based on each object's rebound from a surface is comprised of three main functions: 1) controlling the object's path of motion to incur a natural rebound of the object from a surface of known properties, 2) acquiring a plurality of measurements of the object's position as it undergoes it's response to impacting the surface, and 3) computing the maximum rebound distance achieved from position measurements for use in selecting which independent sorting space should be activated to receive the object as it proceeds in motion.

The method is initially to put a ball 1 into operation by a user or automated ball feeding system 11 which proceeds to drop objects 1 (e.g. tennis balls) one-after-the-other in a controlled manner from a set height 60 (e.g., 100 inches, 254 cm per ITF standard) onto an unyielding surface 20 (smooth granite or concrete per ITF standard) such that each ball rebounds up to a volume measurement space 37 where a collimated light source 36 projects the ball's shadow 3 onto a two dimensional projection screen 33 to be scanned by a video sensor 30 coupled to a computing device 31 which records a series of quantified spatial measurements from the ball shadow image data taken, which are then used to determine the ball's peak rebound height attained 2 which in turn determines to which sort group the ball 1 belongs, then sets the appropriate timing to open one of several sorting gates 40 positioned below the ball representing a sort group, such that the sorting gate is opened sufficiently prior to the ball falling to it, resulting in the ball being re-directed out the determined sorting pathway 63. Sorting gates 40 are arranged peripherally around the ball free-fall area such that only one can be opened at a time and as each is opened creates one and only one exit space through which the ball 1 can be directed to pass. Containers may be placed at or under each sorting exit to catch balls as they exit.

In cases of failure to acquire a valid measurement or failure to re-direct the ball out a sorting pathway 63, the impact surface 20 is shaped so as to allow the ball to fall through the no-sort exit 40 rather than being sorted, thus being no hindrance to subsequent operations.

The next ball is set in the start position by an object dropper 10 (either mechanically or manually) during the sorting operation of the previous ball and the cycle is repeated by dropping the next ball as soon as the previous ball has cleared the path and the sorting gate 40 has returned to closed position. As this process repeats, the number of balls thus dropped and directed into each sorting group are counted by the computing device 31, and relevant data for each ball is recorded. The computing device 31 further makes various status indications available visibly or audibly to aid in monitoring the state of operation, pauses operation when sort counts reach set thresholds so that sort collection bins 41 can be emptied or replaced, and stops the process in the event of various potential malfunctions or to terminate operation when all available balls have been processed.

An embodiment acquires a plurality of measurements of each object's rebound position and decides on which sorting space to direct the object within the finite time available before the object descends after its rebound to the sorting gate area. In an embodiment, the measurements of each objects rebound position may be taken after a first rebound. However, the measurements may also be taken after the ball rebounds more than once. Such embodiment may include the following steps to perform this task.

1) directing a light source with optics aligned to produce near-parallel light rays through the measurement space causing the object's shadow to be projected onto a screen at one side of the measurement space opposite the light source, such that the object's shadow is vertically aligned with the object's actual height regardless of where the object is positioned horizontally within the measurement space;
2) positioning the sensor to detect light levels emitted from discrete points on the projection screen;
3) scanning the projection screen rapidly enough to trace the object shadow's motion while the object ascends to a peak, in order to determine the location of the shadow with sufficient spatial accuracy with respect to its actual peak height above the impact surface;
4) setting sensor modes and configuration for lowest required data rates;
5) reading the minimally needed number of bits of the sensor's digital image data to realize necessary imaging resolutions and scan fidelity;
6) counting single bit data pixels in horizontal scans comparing to calibrated thresholds to determine when object shadow is present verses background;
7) detecting moving shadow edges by scanning downward as the shadow decelerates upward to a peak and applying a row-by-row random-walk algorithm to catch the highest point of the bottom of the shadow;
8) tracking measurement results across multiple image frames to determine the time when the peak rebound distance has occurred, and using the determined time when the peak rebound height has occurred to synchronize the opening of sorting gates with the subsequent position of the objects as they fall from peak;
9) checking for invalid measurements as may be detected from the received scan data, to take alternate action.

This method may also be applied to a type of object 1 which does not rebound away from a stationary surface 20 following impact with the surface, i.e., there is no subsequent path of motion following impact, rather the object remains in contact with the surface before being re-directed based on some other property (for example coefficient of restitution or COR). This is the "null case" where rebound height=0 which is valid in the context of the embodiment as it too involves taking a plurality of measurements of the object's response to impact. This case would require a different sorting embodiment to move the object into a sort space, and may require re-positioning of the sensor at or near the impact surface, but the remainder of the embodiment specified herein remains applicable. Such a case might be the best mode for balls like shot puts that don't bounce per se, but may be required to absorb the energy of impact (i.e. having a very low COR when landing on certain surfaces). This case may also be relevant (or at the least more practical) to the inverted embodiment described below, where a surface designed to dampen or prevent an object's rebound is being subjected to test.

This embodiment may be inverted in terms of the object in motion 1 becoming the calibrated impact surface and the impact surface 20 becoming the object being measured and sorted. The inverted embodiment is used to sort various targeted surfaces based on the measured characteristics of a calibrated object rebounding from the surfaces. For example, the measured response of a calibrated ball dropped onto a plurality of court surfaces moved into position as the ball is cycled repeatedly through each drop. This embodiment would require a modified ball feeding mechanism to return the calibrated ball to the drop mechanism each cycle (rather than sorting it), and would require an embodiment to move a plurality of surface samples into the drop target space in a one-by-one fashion. Sorting of the measured surface responses would entail keeping track of each sample surface (perhaps by count or some form of indexing) such that each measurement is associated to a corresponding sample surface. In such a case grading of each sample is achieved by assigning the recorded measurement data for each trial sample to a predetermined grade.

The foregoing description, for purpose of explanation, has been described with reference to specific embodiments. However, the illustrative discussion above are not intended to be exhaustive or to limit the invention to the precise forms disclosed. Many modifications and variations are possible in view of the above teachings. The embodiments were chosen and described in order to best explain the principle of the invention and its practical applications, to thereby enable others skilled in the art to best utilize the invention and various embodiments with various modifications as are suited to the particular use contemplated.

The invention claimed is:

1. An automatic sorting apparatus based on objects' rebound from a surface, comprising:
    an object holder to hold and drop an object vertically downside with a force of gravity;
    a rebound impact surface disposed vertically downside of the object holder;
    a rebound height sorting sensor configured to measure an apex of a rebound of the object;
    a light source;
    a projection screen; and
    a sorter configured to sort the object based on the apex of the rebounded object,
    wherein the light source projects the object on the projection screen, and the rebound height sorting sensor detects the apex of the rebound of the object based on positions of a shadow of the object on the projection screen.

2. The automatic sorting apparatus of claim 1, further comprising an automated object feeding system configured to feed objects to the object holder one-after-the-other when a path from the object holder to the rebound impact surface is clear.

3. The automatic sorting apparatus of claim 1, wherein the object holder comprises a cylinder that holds the object by exerting an attractive upward force on the object to prevent the object from falling down and that releases the object to fall freely.

4. The automatic sorting apparatus of claim 1, wherein a top of the rebound impact surface is flat for the object to vertically rebound, and a side of the rebound impact surface is a conical shape so that the object's subsequent path proceeds to a no-sort exit space when the sorter does not sort the object.

5. The automatic sorting apparatus of claim 1, wherein the rebound height sorting sensor measures and records a plurality of the positions of the shadow while the object is in motion.

6. The automatic sorting apparatus of claim 1, wherein the rebound height sorting sensor comprises:
   a video sensor device positioned external to a space where the object rebounds, the video sensor device being configured to measure the plurality of the positions of the shadow; and
   a computing device to calculate the apex of the object's rebound.

7. The automatic sorting apparatus of claim 1, wherein the rebound height sorting sensor of claim 6 further comprises a computing device using the measurement for the apex of the object's rebound acquired by the video sensor device to control the operation and timing of the sorter.

8. The automatic sorting apparatus of claim 1, wherein the light source is aligned to produce light rays to the projection screen at a right angle, the projection screen presents the shadow of the moving object, and the rebound height sorting sensor detects moving shadow edges by tracking the scanned edges as the shadow decelerates upward to the apex and applying a row-by-row random-walk algorithm to catch the apex of a bottom of the shadow.

9. The automatic sorting apparatus of claim 1, wherein the light source emits light rays upward from a place around the rebound impact surface, and the light rays from the light source are reflected through a mirror aligned to project the light rays on the projection screen at a right angle.

10. The automatic sorting apparatus of claim 1, wherein the sorter comprises at least one gate configured to open according to the apex detected by the height sorting sensor, the at least one gate being positioned to accept the object after the object rebounds from the rebound impact surface.

11. The automatic sorting apparatus of claim 10, wherein each gate has a rigid flap mounted by at least one spring loaded hinge.

12. The automatic sorting apparatus of claim 11, wherein an electric push solenoid forces the rigid flap to open the gate against the resistive force of the spring loaded hinge which will then automatically close the gate after the rigid flap has reached a maximum position, wherein the opening and closing of the gate by the push solenoid is timed according to the computed apex of the object and the time needed for the object to free-fall to the gate location.

13. A method for automatically sorting objects based on the objects' rebound from a surface, comprising:
   dropping an object;
   emitting light rays to the rebounded object on a project screen at a right angle;
   acquiring a plurality of the object's positions based on positions of a shadow of the rebounded object on the project screen;
   detecting moving shadow edges by scanning the moving shadow edges;
   determining a peak rebound position of the object based on the detected edges; and
   directing the rebounded object into a selected space of a plurality of independent sorting spaces, wherein the object is directed to the selected space based on the determined peak rebound position of the object, and a gate directing to the selected space is activated at a proper time according to the peak rebound position.

14. The method for automatically sorting objects of claim 13, wherein the object is controlled to fall vertically downward with a force of gravity and to rebound naturally upward.

15. The method for automatically sorting objects of claim 13, further comprising: determining the selected space of the plurality of independent sorting spaces based on the peak rebound position of the object before completion of an object's second natural fall.

16. The method for automatically sorting objects of claim 13, further comprising: setting rebound height range thresholds, and assigning the range thresholds to the plurality of independent sorting spaces, wherein rebound grades are mapped to the plurality of independent sorting spaces.

17. The method for automatically sorting objects of claim 16, wherein directing the object into the selected space of the plurality of independent sorting spaces based on the peak rebound position of the object and the rebound height range thresholds.

18. The method for automatically sorting objects of claim 13, wherein the plurality of the object's positions are acquired with a video sensor device positioned external to a space to measure the plurality of the object's positions.

19. The method for automatically sorting objects of claim 18, wherein the peak rebound position of the object is determined based on frame data of the video sensor.

20. The method for automatically sorting objects of claim 14, further comprising aligning an impact surface so that the object impacts the surface on a first vertical descent, and then due to random displacement from true vertical from a rebound the object passes out the surface on a subsequent second descent without hindering a motion of subsequently dropped objects.

21. The method for automatically sorting objects of claim 15, further comprising controlling the plurality of independent sorting spaces using sorting gates to open one sorting gate at a time to redirect the object to the selected space.

22. The method for automatically sorting objects of claim 16, further comprising:
   setting sensor modes and configurations to complete the highest possible number of scanned frames while object crests at its highest point, while sending the least possible data to a computing device while still attaining required image resolution;
   directing a light source with optics aligned to produce generally parallel light rays through a measurement space causing an object's shadow to be projected onto a screen at one side of the measurement space opposite the light source, such that the object's shadow appears vertically aligned with the object's actual height regardless of where the object is positioned horizontally within the measurement space;
   positioning a video sensor in relation to the screen such that the video sensor focuses on the screen such that the computing device can correlate each vertical scan line from the video sensor to a corresponding height measurement for the object;
   reading a minimally needed number of bits of video sensor's digital image data while still realizing necessary imaging resolutions and scan fidelity to detect the object shadow;
   counting single bits from the sensor's horizontal scan data as pixels, comparing the count to calibrated thresholds to detect presence of the object shadow and distinguish the object shadow from screen edge and background shadow;

detecting moving shadow edges as the shadow decelerates upward to a peak by evaluating each line of pixel count data downward as it arrives in each video frame and applying a row-by-row random-walk algorithm to catch the highest point of the bottom of the shadow;

analyzing measurement results across multiple image frames to determine the time when the peak rebound height has occurred, and using the determined time when the peak rebound height has occurred to synchronize the opening of sorting gates with the subsequent position of the objects as they fall from peak;

checking for invalid measurements as may be indicated in the computed peaks for each frame, taking alternate action if peaks do not represent natural object motion; and minimizing software processing load to maintain near-real-time operation such that ail critical measurement and timing functions are not disrupted or delayed.

23. An automatic sorting apparatus based on objects' rebound from a surface, comprising:
- a frame;
- a rebound impact surface disposed within the frame vertically downside of an object dropper or a top of the frame;
- a rebound height sorting sensor configured to measure an apex of a rebound of the object;
- a controller configured to determine a level of quality of the object based on the measurement of the apex of the rebound of the object collected from a sensor, wherein the controller controls the object to drop when the object is a first object to be dropped or a previous object is cleared between the rebound impact surface and the point from which the object is dropped,
- a light source; and
- a projection screen,
- wherein the light source projects the object on the projection screen, and the rebound height sorting sensor measures the apex of the rebound of the object based on the height of a shadow image of the object.

24. The automatic sorting apparatus of claim 23, further comprising
- an object holder attached at a top of the frame and configured to hold and release the object vertically downside with a force of gravity; and
- a sorting mechanism configured to sort the object based on the apex of the rebound of the object.

* * * * *